United States Patent
Fujii et al.

(10) Patent No.: US 7,755,044 B2
(45) Date of Patent: Jul. 13, 2010

(54) APPARATUS FOR WORKING AND OBSERVING SAMPLES AND METHOD OF WORKING AND OBSERVING CROSS SECTIONS

(75) Inventors: Toshiaki Fujii, Chiba (JP); Haruo Takahashi, Chiba (JP); Junichi Tashiro, Chiba (JP)

(73) Assignee: SII Nano Technology Inc., Chiba (JP)

( * ) Notice: Subject to any disclaimer, the term of this patent is extended or adjusted under 35 U.S.C. 154(b) by 338 days.

(21) Appl. No.: 12/047,013

(22) Filed: Mar. 12, 2008

(65) Prior Publication Data

US 2008/0224198 A1    Sep. 18, 2008

(30) Foreign Application Priority Data

Mar. 12, 2007  (JP)  ............................. 2007-061472
Mar. 7, 2008  (JP)  ............................. 2008-058467

(51) Int. Cl.
*G21K 5/04*  (2006.01)
*G21K 5/10*  (2006.01)
(52) U.S. Cl. .................. 250/307; 250/491.1; 250/492.2
(58) Field of Classification Search ................. 250/307, 250/491.1, 492.21
See application file for complete search history.

(56) References Cited

U.S. PATENT DOCUMENTS

| | | | |
|---|---|---|---|
| 5,798,529 A * | 8/1998 | Wagner | 250/492.21 |
| 6,042,736 A * | 3/2000 | Chung | 216/33 |
| 7,095,021 B2 * | 8/2006 | Shichi et al. | 250/307 |
| 7,326,942 B2 * | 2/2008 | Shichi et al. | 250/492.21 |
| 7,354,500 B2 * | 4/2008 | Yoshioka et al. | 156/345.39 |
| 7,368,729 B2 * | 5/2008 | Shichi et al. | 250/442.11 |
| 2002/0017619 A1 * | 2/2002 | Hirose et al. | 250/492.3 |
| 2003/0150836 A1 * | 8/2003 | Tsung et al. | 216/67 |

FOREIGN PATENT DOCUMENTS

JP   5-28950 A    2/1993
JP   3117836 B    10/2000

* cited by examiner

*Primary Examiner*—Evan Pert
(74) *Attorney, Agent, or Firm*—Brinks Hofer Gilson & Lione

(57) ABSTRACT

The apparatus for working and observing samples comprises a sample plate on which a sample is to be placed; a first ion beam lens barrel capable of irradiating a first ion beam over a whole predetermined irradiation range at one time; a mask that can be arranged between the sample plate and the first ion beam lens barrel, and shields part of the first ion beam; mask-moving means capable of moving the mask; a charged particle beam lens barrel capable of scanning a focused beam of charged particles in the range irradiated with the first ion beam; and detection means capable of detecting a secondarily generated substance.

11 Claims, 9 Drawing Sheets

APPARATUS FOR WORKING AND OBSERVING SAMPLES AND METHOD OF WORKING AND OBSERVING CROSS SECTIONS

RELATED APPLICATIONS

This application claims priority under 35 U.S.C. §119 to Japanese Patent Application Nos. JP2007-061472 filed Mar. 12, 2007 and JP2008-058467 filed Mar. 7, 2008, the entire contents of which are hereby incorporated by reference.

BACKGROUND OF THE INVENTION

This invention relates to an apparatus for working and observing cross sections of samples by irradiating the samples with an ion beam, and a method of working and observing cross sections.

A method of observing cross sections has heretofore been carried out by forming a cross section in the sample by etching the sample by the irradiation with an ion beam. For example, a method has been proposed for forming a cross section by using a focused ion beam lens barrel and by irradiating a focused ion beam on a predetermined position for forming the cross section without using a mask (e.g., see Japanese Patent No. 3117836). According to this method, the cross section that is formed is irradiated with a focused ion beam at a low acceleration voltage and with a small current, or a scanning electron microscope is also used or is separately constituted to irradiate an electron beam, and the cross section is observed by detecting the generated secondary electrons. There has further been proposed a method of effecting the finish working again by the irradiation with a focused ion beam by using a mask after a predetermined position is etched by the irradiation with the focused ion beam (see, for example, JP-A-5-28950).

According to the methods of Japanese Patent No. 3117836 and JP-A-5-28950 which execute the working by using the focused ion beam, the working precision can be improved but limitation is imposed on the amount of electric current for irradiation. Therefore, when a large cross section of a side of about 100 μm is to be worked such as of electronic parts, the working time of about several tens of hours is required. In this case, it can be contrived to work the cross section by a mechanical method without, however, able to maintain precision of position on the cross section. When the cross section is to be observed, further, a device for observation must be separately provided.

The present invention was accomplished in view of the above circumstances, and provides an apparatus for working and observing samples capable of efficiently working and observing even large cross sections of electronic parts maintaining positional precision of cross sections, and a method of working and observing cross sections.

SUMMARY OF THE INVENTION

In order to solve the above problems, the present invention proposes the following means.

The apparatus for working and observing samples of the invention comprises a sample plate on which a sample is to be placed; a first ion beam lens barrel capable of irradiating the sample placed on the sample plate with a first ion beam over a whole predetermined irradiation range at one time; a mask that can be arranged between said sample plate and said first ion beam lens barrel, and shields part of said first ion beam; mask-moving means capable of moving the mask on an XY-plane which intersects the direction of the first ion beam lens barrel in which the first ion beam is irradiated nearly at right angles therewith; a charged particle beam lens barrel capable of scanning a focused beam of charged particles in the range irradiated with the first ion beam; and detection means capable of detecting a secondarily generated substance generated by the irradiation of the sample or the mask with the beam of charged particles from the charged particle beam lens barrel.

Further, the method for working and observing a cross section of the invention comprises a mask position-adjusting step of adjusting the position of the edge end of a mask and the position for forming the cross section of the sample by arranging the mask on a sample, and by detecting a secondarily generated substance generated as a result of scanning a focused beam of charged particles; a first cutting step of forming a cross section of the sample at the position for forming the cross section corresponding to the edge end of the mask by etching the sample exposed through the through hole in the mask by irradiating the mask of which the position is adjusted on the sample with a first ion beam over a whole predetermined irradiation range at one time; and a cross section observation step of detecting the secondarily generated substance generated as a result of scanning a focused beam of charged particles on the cross section of the sample.

According to the apparatus for working and observing samples and the method of working and observing cross sections of the present invention, first, the position of an edge end of the mask and the position for forming the cross section of the sample are adjusted by the mask-moving means as the position-adjusting step. Here, a beam of charged particles focused by the charged particle beam lens barrel scans on the mask and on the sample to detect a substance secondarily generated from the mask and the sample by detection means, to correctly grasp the position of the edge end of the mask and, therefore, to precisely adjust the position relative to the position for forming the cross section. Next, as the first cutting step, the sample is etched by the irradiation with the first ion beam from the first ion beam lens barrel to thereby form a cross section of the sample at the position for forming the cross section corresponding to the edge end of the mask. Here, the first ion beam can be irradiated over a whole predetermined irradiation range at one time to efficiently etch the sample. Further, the position at the edge end of the mask is correctly adjusted through the position-adjusting step, and the cross section of the sample is correctly formed at a predetermined position for forming the cross section. In the cross section observation step, therefore, the cross section of the sample is irradiated with the beam of charged particles from the charged particle beam lens barrel, and the secondarily generated substance is detected by the detection means to precisely observe the desired cross section of the sample.

In the apparatus for working and observing samples, further, it is desired that the first ion beam of the first ion beam lens barrel is an inert ion beam.

In the method of working and observing a cross section, further, it is desired that the first cutting step uses a beam of inert ions as the first ion beam.

According to the apparatus for working and observing samples and the method of working and observing cross sections of the present invention, an inert ion beam is irradiated as the first ion beam from the first ion beam lens barrel in the first cutting step to suppress damage to the formed cross section of the sample and, therefore, to form a better cross section of the sample.

In the apparatus for working and observing samples, further, it is desired to provide a second ion beam lens barrel capable of scanning a second ion beam that is focused with an electric current smaller than that for the first ion beam within the range irradiated with the first ion beam.

In the apparatus for working and observing samples, further, it is desired to provide an electron beam lens barrel capable of scanning a focused electron beam within the range irradiated with the first ion beam.

In the method of working and observing a cross section, further, it is desired to provide a second cutting step of etching the surface of the cross section of the sample by scanning a second ion beam focused with an electric current smaller than that for the first ion beam on the cross section of the sample after the first cutting step has been finished, wherein the cross section observation step is executed after the second cutting step has been finished.

In the method of working and observing a cross section, further, it is desired that in the cross section observation step, the cross section of the sample is observed by scanning a focused electron beam on the cross section of the sample.

In the method of working and observing a cross section, further, it is desired that in the cross section observation step, the cross section of the sample is observed by scanning a second ion beam focused with an electric current smaller than that for the first ion beam on the cross section of the sample.

According to the apparatus for working and observing samples and the method of working and observing cross sections of the present invention, a second ion beam focused with a small current is irradiated from the second ion beam lens barrel in the second cutting step after the first cutting step has been finished to form a better cross section of the sample.

In the cross section observation step, further, the cross section of the sample can be favorably observed by using the second ion beam focused with an electric current smaller than that for the first ion beam or the focused electron beam.

It is further desired that the apparatus for working and observing samples is provided with a mask-exchanging mechanism for exchanging the mask with a mask different from the mask arranged in the apparatus for working and observing the samples.

It is further desired that the method of working and observing samples includes the step of exchanging the mask with a mask different from the mask arranged in the apparatus for working and observing samples.

According to the apparatus for working and observing samples and the method of working and observing cross sections of the present invention, the mask can be exchanged with another mask arranged in the apparatus for working and observing samples. In the step of cutting samples, therefore, the mask of which the edge end has deformed due to re-deposition or the like can be exchanged in the apparatus. The mask can be efficiently exchanged without opening the apparatus to the atmosphere and, besides, vacuum can be maintained in the apparatus.

According to the apparatus for working and observing samples of the invention, a large cross section can be efficiently worked by using the first ion beam lens barrel and the mask, and a positional precision of cross section can be maintained relying upon the charged particle beam lens barrel and the detection means, making it possible to observe a desired cross section of the sample maintaining precision.

According to the method of working and observing cross sections of the invention, a large cross section can be efficiently worked maintaining a positional precision of cross section relying upon the position-adjusting step and the first cutting step, making it possible to observe a desired cross section of the sample maintaining precision

DETAILED DESCRIPTION OF THE PREFERRED EMBODIMENTS

First Embodiment

Figure 1:
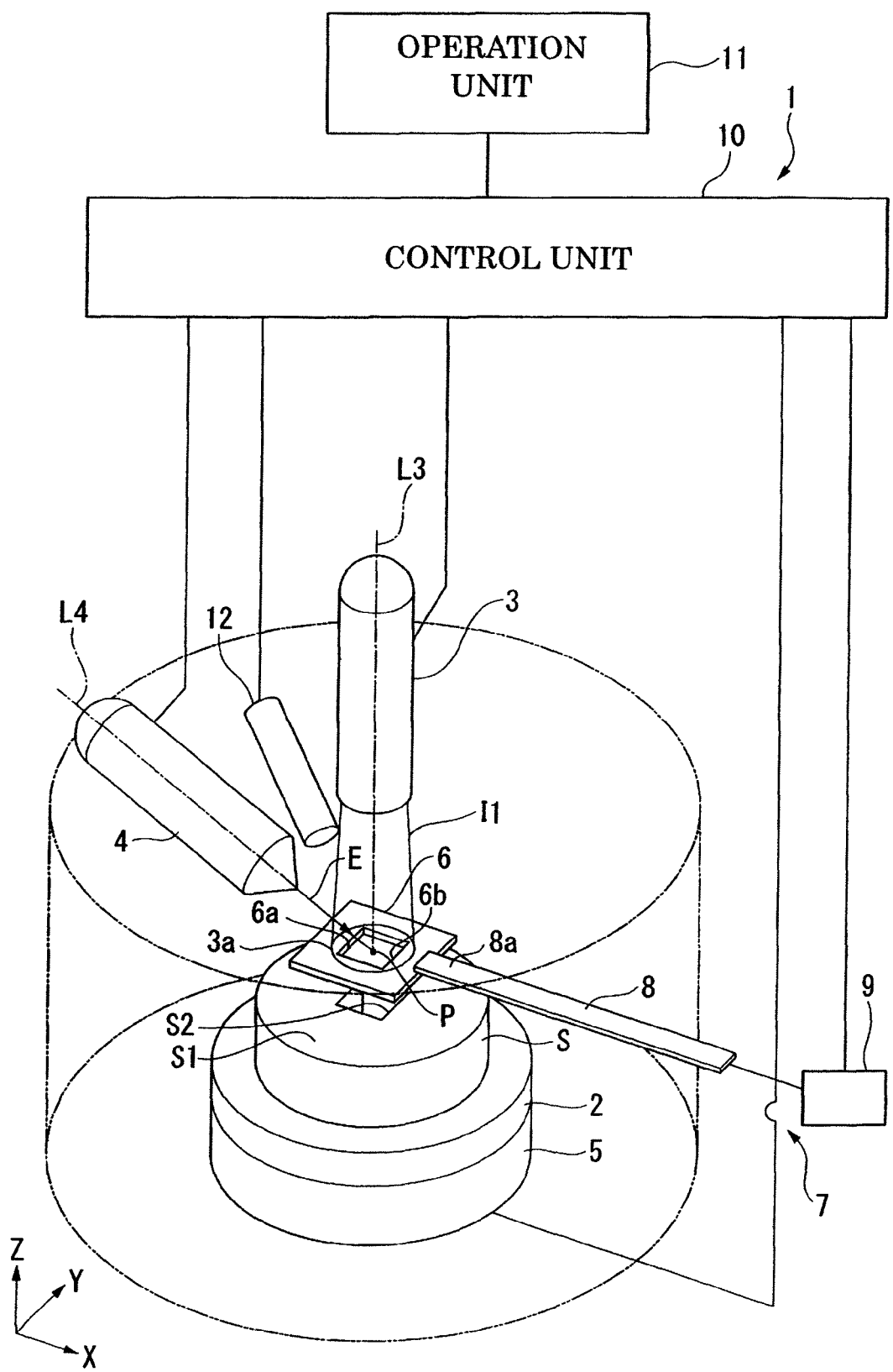
FIG. 1 is a view illustrating the constitution of an apparatus for working and observing samples according to a first embodiment of the invention.

FIG. 1 illustrates a first embodiment according to the invention.

Referring to FIG. 1, an apparatus 1 for working and observing samples includes a sample plate 2 for placing a sample S, a first ion beam lens barrel 3 capable of irradiating a first ion beam I1, and an electron beam lens barrel 4 which is a charged particle beam lens barrel capable of irradiating an electron beam E focused as a charged particle beam. A five-axis stage 5 is provided at a lower portion of the sample plate 2. The five-axis stage 5 is capable of sliding the sample S placed on the sample plate 2 in a Z-axis direction in which the first ion beam I1 is irradiated, and in an X-axis direction and in a Y-axis direction nearly at right angles with the Z-axis, and is allowed to rotate about the Y-axis and the Z-axis.

If described in further detail, the first ion beam lens barrel 3 includes an argon ion source and a xenon ion source as ion sources, and is capable of irradiating an inert ion beam as the first ion beam I1. In this embodiment, an argon ion beam can be irradiated as the first ion beam I1. The first ion beam lens barrel 3 is capable of irradiating the first ion beam I1 over a whole predetermined irradiation range 3a at one time with the center axis L3 as a center, and the amount of current thereof is as great as, for example, of the order of microamperes. The center axis L4 of the electron beam lens barrel 4 is so arranged as to intersect the center axis L3 of the first ion beam lens barrel 3 at a point P of intersection, and the electron beam lens barrel 4 is capable of scanning the electron beam E in the irradiation range 3a of the first ion beam lens barrel 3 with the center axis L4 as a center. In FIG. 1, the mask 6 and the sample S are drawn spaced more apart than they really are. In practice, however, the mask 6 is very close to the surface of the sample S, and an intersecting point P is close to the surface of the sample.

A mask 6 is provided between the first ion beam lens barrel 3 and the sample S. The mask 6 is nearly of the shape of a plate and is selected to be larger than the irradiation range 3a so as to shield the first ion beam I1. The mask 6 has a through hole 6a formed therein in a shape depending upon the object of machining. In this embodiment, the through hole 6a is formed in, for example, a rectangular shape, and its edge end 6b is set in a size that meets the width of cross section necessary for the observation that will be described later. As will be described later, by using the first ion beam I1 and the mask 6, the cross section S2 of the sample formed at a position facing the edge end 6b is observed by being irradiated with the electron beam E. It is, therefore, desired that the direction of the through hole 6a in the mask 6 is such that the edge end 6b is in a direction nearly at right angles with the direction in which the electron beam E is irradiated as viewed from the upper side. The mask 6 is provided with mask-moving means 7 enabling the mask 6 to be retracted from over the sample S. The mask-moving means 7 includes a manipulator 8 which is nearly in the shape of a rod and is fixed at an end 8a thereof to the mask 6, and a drive unit 9 capable of moving the manipulator 8 on an XY-plane nearly at right angles with the center axis L3 of the first ion beam lens barrel 3.

The above first ion beam lens barrel 3, electron beam lens barrel 4, five-axis stage 5 and drive unit 9 are connected to a control unit 10. Being controlled by the control unit 10, the first ion beam lens barrel 3 and the electron beam lens barrel 4 adjust the acceleration voltage and the amount of electric current, and irradiate the first ion beam I1 and the electron beam E, respectively. Being controlled by the control unit 10, further, the five-axis stage 5 adjusts the position of the sample S in the X-axis direction, in the Y-axis direction and in the Z-axis direction and, further, adjusts the angle of the sample S about the Y-axis and about the Z-axis. Being controlled by the control unit 10, further, the drive unit 9 moves the manipulator 8 thereby to adjust the position of the mask 6 as well as to retract the mask 6 from over the sample S. Further, an operation unit 11 is connected to the control unit 10 enabling the operator to operate the first ion beam lens barrel 3, electron beam lens barrel 4, five-axis stage 5 and drive unit 9.

The apparatus 1 for working and observing samples is, further, equipped with a secondary electron detector 12 for detecting secondary electrons as detection means for detecting a secondarily generated substance that generates upon irradiating the sample 2 and the mask 6 with the electron beam E. The secondary electron detector 12 is connected to the control unit 10. Based on the results detected by the secondary electron detector 12, the control unit 10 forms images of the sample S and the mask 6, and outputs them to a monitor that is not shown, or obtains data related to the positions from the image data.

Figure 2:
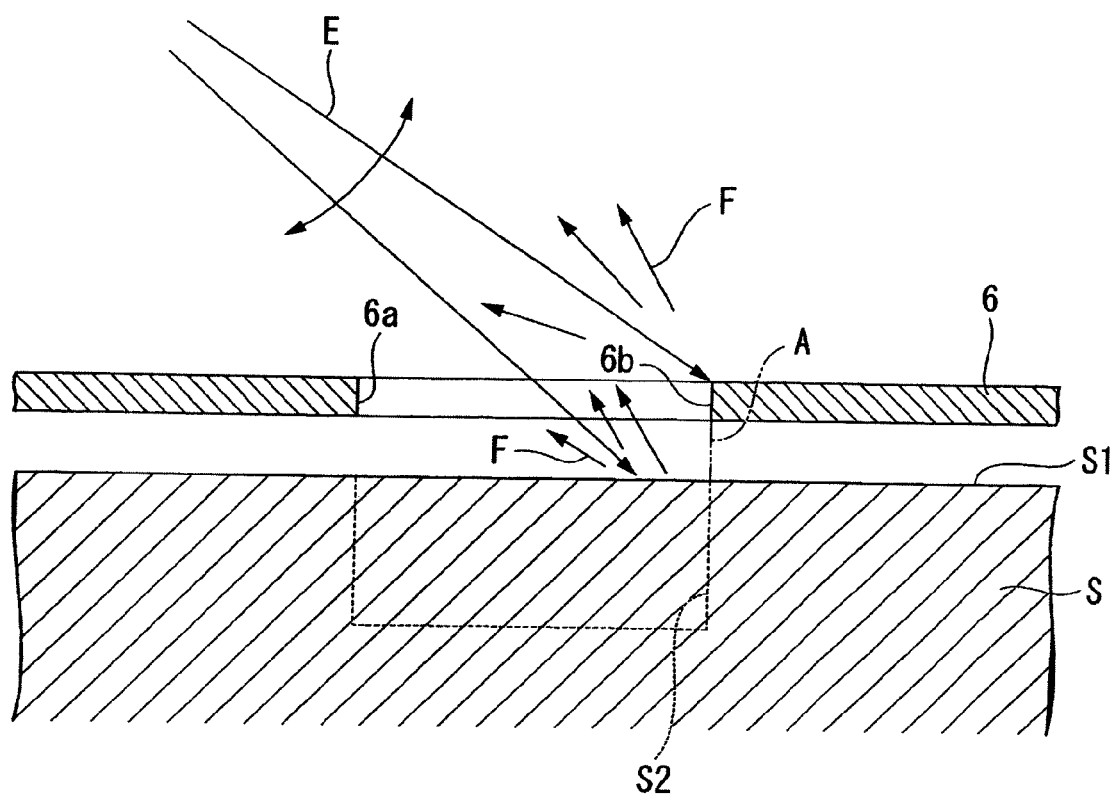
FIG. 2 is a view illustrating a step of adjusting the mask position according to the first embodiment of the invention.

Next, described below is a method of working and observing cross sections by forming a cross section S2 of sample at a predetermined position A where a cross section of the sample S is to be formed by using the apparatus for working and observing samples. Referring, first, to FIG. 1, the sample S is placed on the sample plate 2, and the position of the sample S is adjusted by driving the five-axis stage 5 under the control of the control unit 10. Next, as a step of adjusting the mask position, the mask 6 is arranged on the sample S to adjust the position thereof. That is, as shown in FIG. 2, the drive unit 9 of the mask-moving means 7 is driven under the control of the control unit 10, and the position of the mask 6 fixed to the end 8a of the manipulator 8 is so adjusted that the edge end 6b of the through hole 6a comes nearly into agreement with the position A where the cross section is formed as viewed from the upper side. At this moment, the control unit 10 drives the electron beam lens barrel 4 to scan the electron beam E near the edge end 6b of the through hole 6a and near the surface S1 of the sample, while the secondary electrons F generated from the mask 6 and the sample S are detected by the secondary electron detector 12, correspondingly, to form images thereof. Based on the images, the position is adjusted while making sure if the position A forming the cross section is nearly in agreement with the edge end 6b of the mask 6. Therefore, the position of the edge end 6b of the through hole 6a can be correctly grasped, and the position of the edge end 6b can be precisely adjusted relative to the position A forming the cross section. The position may be adjusted manually by the operator by using the operation unit 11 while making sure the images, or the position may be automatically adjusted by the control unit 10 in accordance with the data related to the position obtained from the image data.

Next, as the first cutting step, the sample S is etched for forming the cross section S2 at a position corresponding to the position A for forming cross section of the sample S. Namely, referring to FIG. 3, the control unit 10 drives the first ion beam lens barrel 3 to irradiate the first ion beam I1. The first ion Beam I1 is irradiated over the whole irradiation range 3a at one time, shielded by the mask 6, and a portion thereof passes through the through hole 6a to etch the sample S. Therefore, the sample S is etched at a position and in a shape corresponding to the through hole 6a, and the cross section S2 is formed in the sample at a position corresponding to the edge end 6b.

Figure 4:
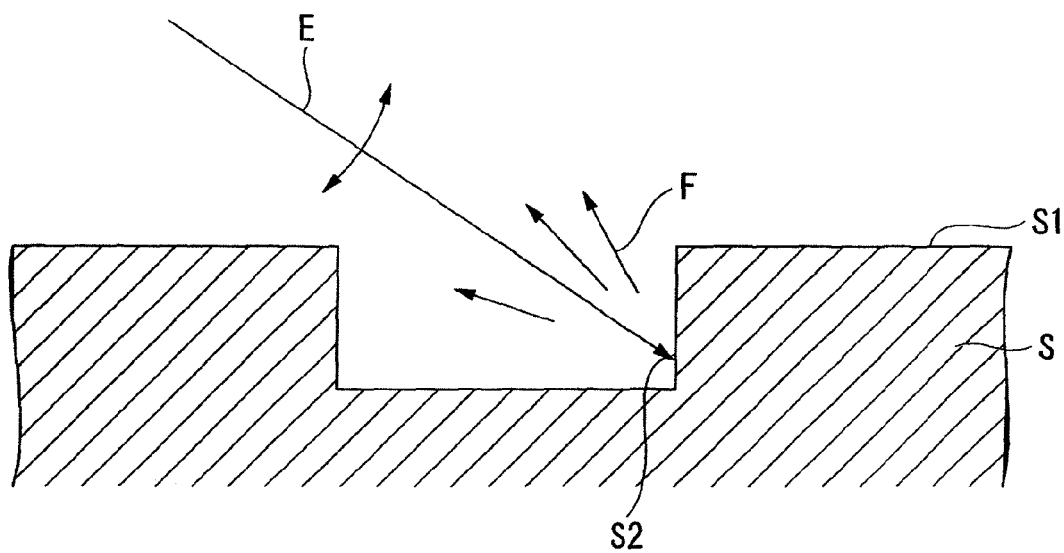
FIG. 4 is a view illustrating a cross section observation step according to the first embodiment of the invention.

Next, as the cross section observation step, the cross section S2 formed in the sample is observed. Referring, first, to FIG. 4, the control unit 10 drives the drive unit 9 in the mask-moving means 7 to retract the mask 6 from over the sample S. The control unit 10, then, drives the electron beam lens barrel 4 to scan the electron beam E over a range of the cross section S2 of the sample. The secondary electrons F generated from the cross section S2 of the sample correspondingly are detected by the secondary electron detector 12. Based on the detected results, the control unit 10 forms an image of the cross section S2 of the sample enabling the cross section S2 of the sample to be observed.

Through the first cutting step as described above, the first ion beam I1 is irradiated by the first ion beam lens barrel 3 over the whole irradiation range 3a at one time to efficiently etch the sample S being corresponded to the through hole 6a of the mask 6. The position of the edge end 6b of the mask 6 has been adjusted by the electron beam lens barrel 4 and the secondary electron detector 12 through the mask position-adjusting step. Therefore, the cross section S2 can be correctly formed in the sample at the position A for forming cross section. Therefore, the cross section can be precisely and efficiently formed in the sample at a desired position for forming cross section even when forming a large cross section of a side of about 100 μm in a large sample such as solder balls and printed wiring boards. Upon being provided with the electron beam lens barrel 4 and the secondary electron detector 12, further, the desired cross section S2 of the sample can be precisely observed through the cross section observation step and, besides, the throughput can be improved from the working through up to observation without the need of providing any separate device for observation. In this embodiment, further, the first ion beam I1 irradiated from the first ion beam lens barrel 3 is an argon ion beam which is an inert beam. This makes it possible to form the favorable cross section S2 on the sample suppressing damage to the cross section S2 of the sample caused by the irradiation with an ion beam. Without using gallium ions, further, the surrounding environment is not fouled lending the method well suited for observing cross sections such as of semiconductor integrated circuits on a production line.

Figure 7A:
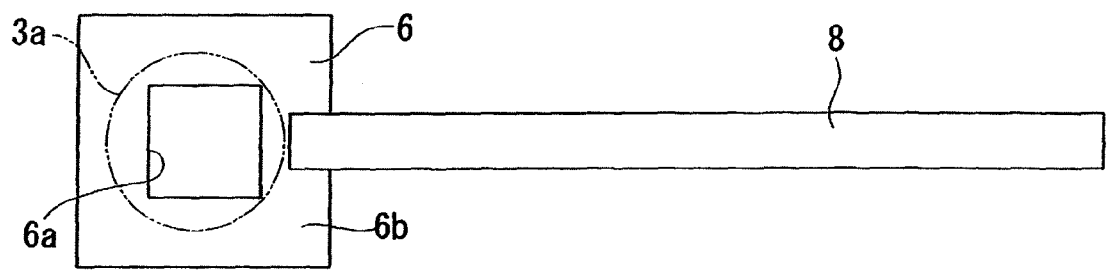
FIGS. 7A-7C are diagrams illustrating the mask shapes according to the first embodiment of the invention.
Figure 7B:
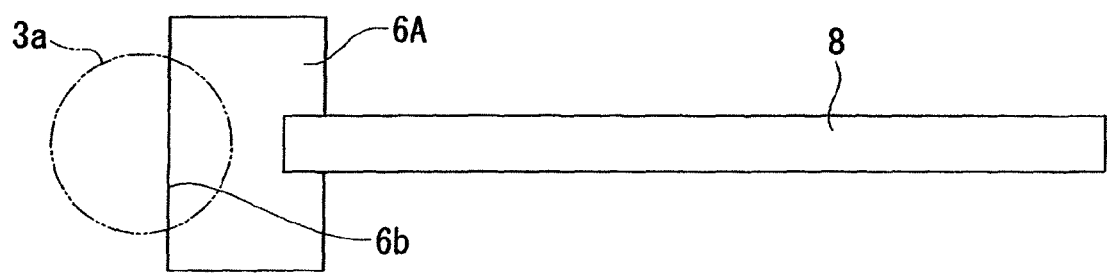
Figure 7C:
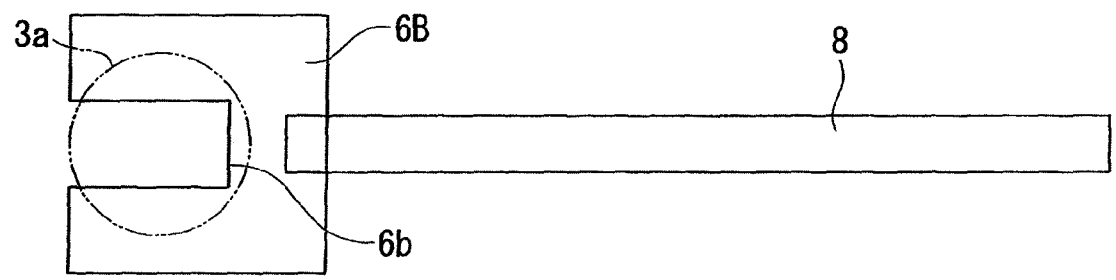

In the foregoing was described the mask 6 fixed to the end 8a of the manipulator 8 and having the through hole 6a formed therein. However, there may be employed the mask 6 of any other shape if it is capable of shielding part of the first ion beam I1. FIGS. 7A-7C are top views of the mask fixed to the manipulator 8. In FIGS. 7a, 7b and 7c, circles represented by two-dot chain lines are the portions irradiated with the ion beam. FIG. 7A illustrates the mask having the through hole 6a formed therein described above. In this case, the through hole 6a of the mask 6 is smaller than the range irradiated with the ion beam, and the mask is larger than the range irradiated with the ion beam. The mask 6A may be, for example, of nearly the shape of a plate as shown in FIG. 7B. Or, there may be used the plate-like mask 6B of the U-shape as shown in FIG. 7C.

In the step of cutting the sample S, if the working is repeated many times by using the same mask 6, the substance sputtered by the irradiation with the first ion beam I1 impinges upon the mask 6 and deposits (re-deposition) on the mask 6. Or, the surrounding gaseous molecules are decomposed by the secondary electrons generated as the first ion beam I1 impinges on the mask 6, and the decomposed substance deposits on the mask 6 causing the mask 6 to be deformed. Further, the mask 6 is also deformed by being etched with the first ion beam 11. In particular, the edge end 6b that is deformed of the mask 6 affects the shape of the sectional surface S2 of the formed sample. Therefore, the mask 6 after used for the working many times must be exchanged by another mask.

Figure 8:
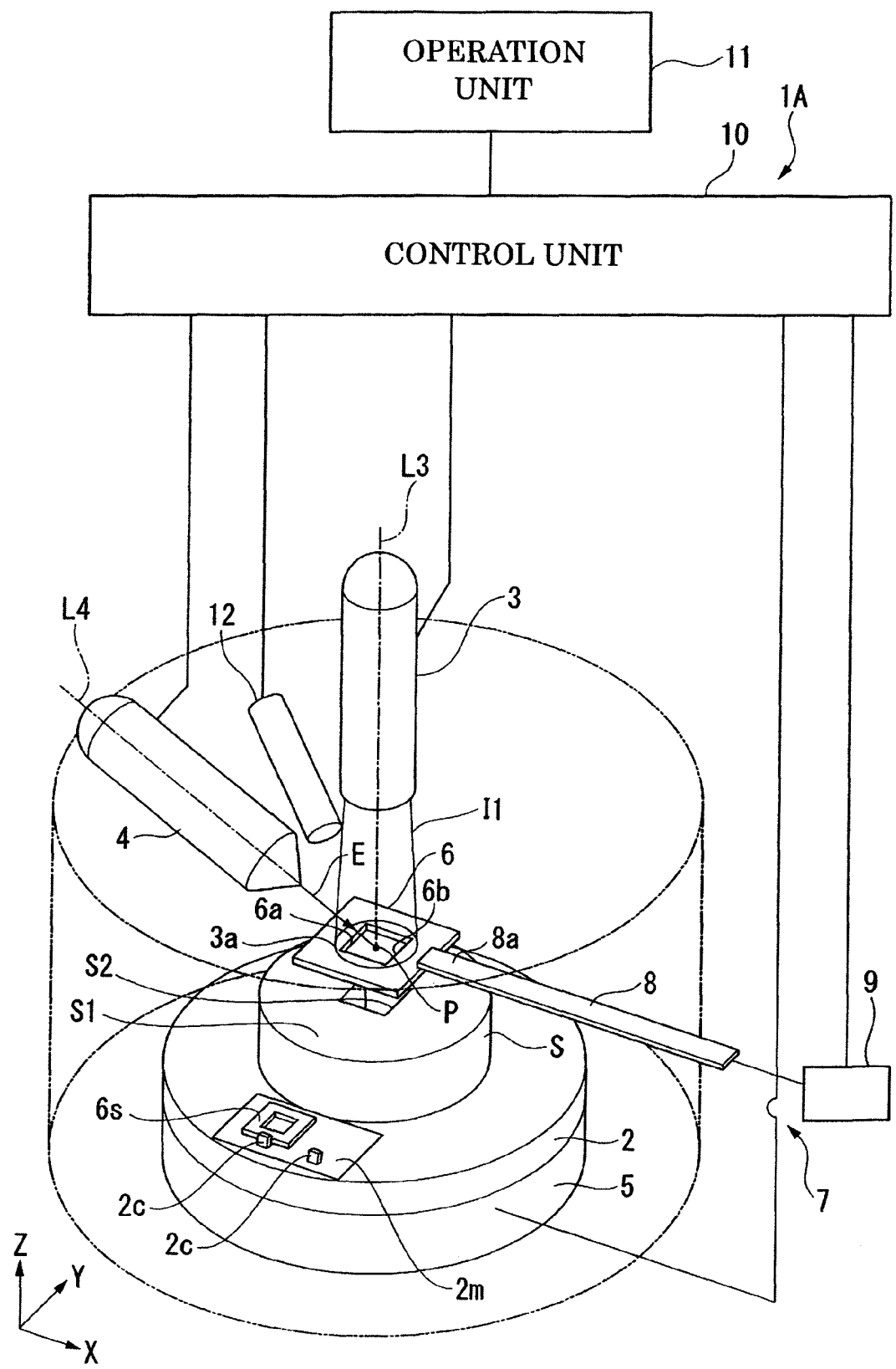
FIG. 8 is a view illustrating the constitution of the apparatus for working and observing samples according to the first embodiment of the invention.

FIG. 8 is a view illustrating the constitution of the apparatus 1A for working and observing samples equipped with a mechanism for exchanging the mask 6 by a mask 6s for exchange in the apparatus 1 for working and observing samples. The mask 6s for exchange is placed on a mask plate 2m which is the mask-exchanging mechanism. Further, the mask plate 2m is placed on the sample plate 2 and is adjustable for its position. The step of exchanging the mask is carried out according to the following procedure. First, a five-axes stage 5 is so moved that a point on the mask plate 2m comes under around the intersecting point P, so that the mask plate 2m can be observed with an electron beam E. Next, the manipulator 8 is driven to move the mask 6 on the mask plate 2m. The mask 6 is separated away from the manipulator 8 while observing the mask 6 by the irradiation with the electron beam E, and is placed on the mask plate 2m. Next, the sample plate 2 is moved to move the mask 6s for exchange to the intersecting point P. The end 8a of the manipulator 8 is connected to the mask 6s for exchange. The mask can be thus exchanged.

Figure 9:
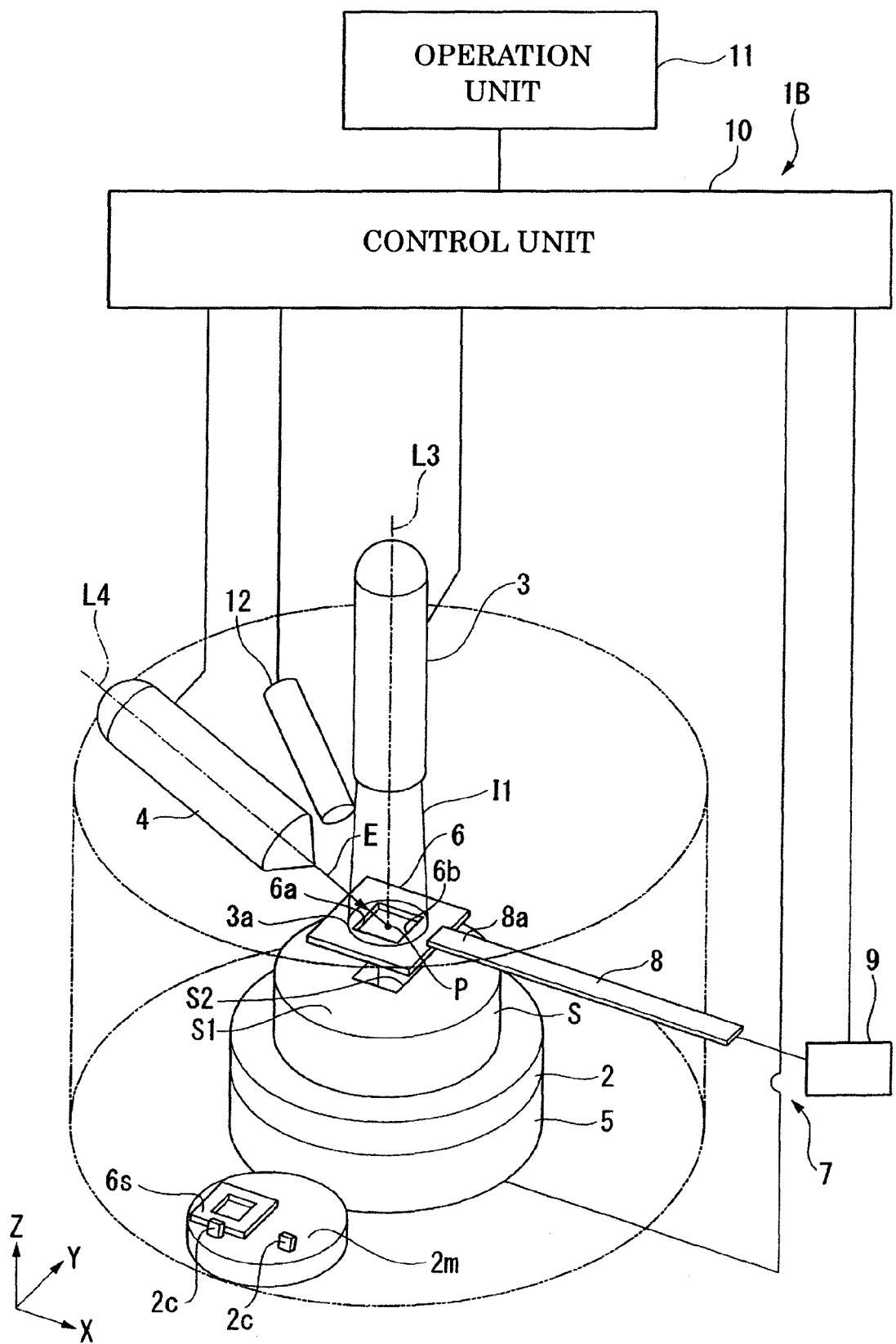
FIG. 9 is a view illustrating the constitution of the apparatus for working and observing samples according to the first embodiment of the invention.
Figure 10B:
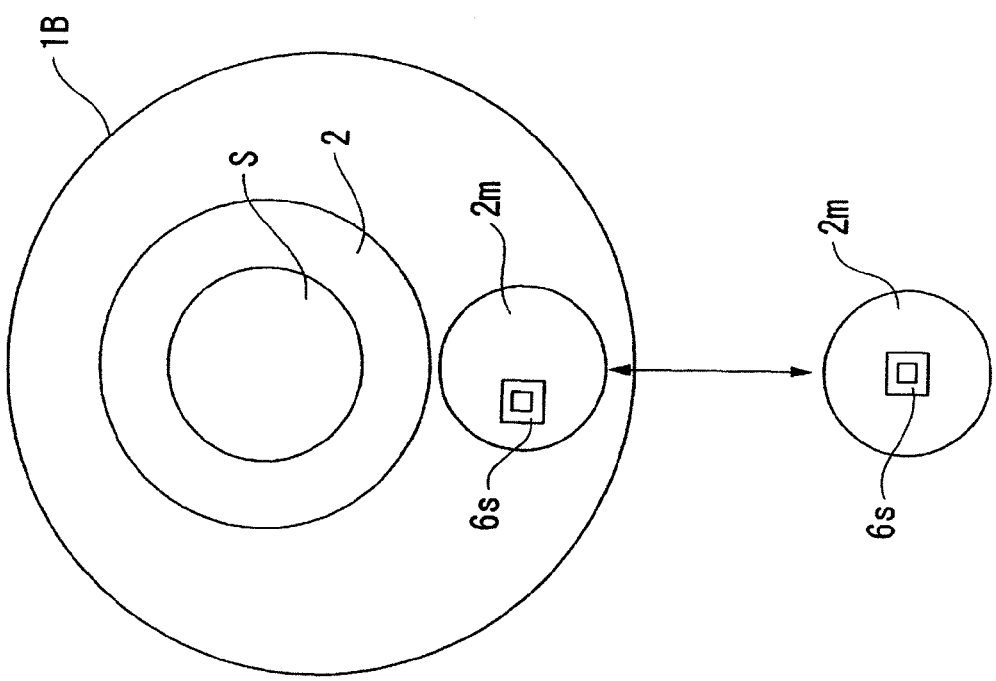
FIGS. 10A-10B are explanation views regarding taking out and putting in of the mask in the apparatus for working and observing samples.
Figure 10A:
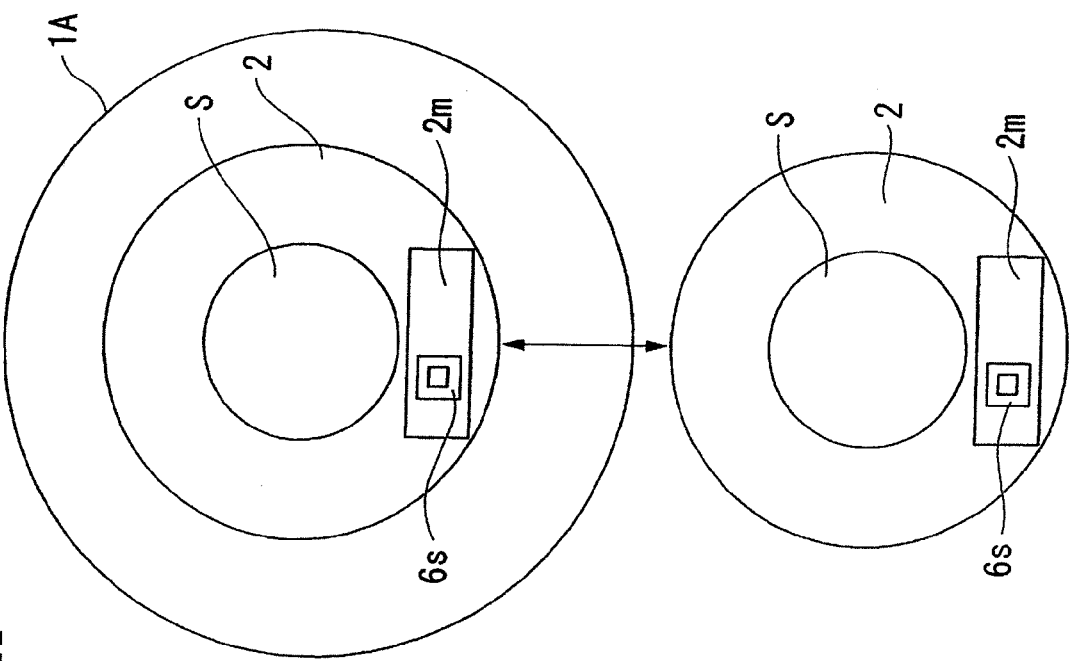

The mask 6 may be separated away from the manipulator 8 by etching using the first ion beam 11. The connection may be attained relying on the deposition that will be described in a second embodiment. As another method, the mask 6 may be fixed onto, or separated away from, the mask plate 2m by using a fitting 2c for attaching/detaching the mask. Here, the mask plate 2m is placed on the sample plate 2 but may be controlled independently of the sample plate 2. In the apparatus 1B for working and observing samples shown in FIG. 9, the mask plate 2m and the sample plate 2 are controlled independently from each other. FIG. 10A is a diagram illustrating the constitution of the apparatus for working and observing samples, wherein the sample plate 2 is controlled with the mask plate 2m being placed thereon. Here, in taking the sample plate 2 in or out of the apparatus 1 for working and observing samples, the mask plate 2m, too, can be taken in or taken out together therewith. FIG. 10B, on the other hand, is a diagram illustrating the constitution of the apparatus for working and observing samples, wherein the sample plate 2 and the mask plate 2m are controlled independently, and the mask plate 2m only can be taken in or taken out of the apparatus for working and observing samples.

By using the above mask-exchanging mechanism, the mask 6 can be exchanged with the mask 6s for exchange in the apparatus 1 for working and observing samples. That is, the mask can be exchanged without the need of taking the mask out of the apparatus 1 for working and observing samples. Therefore, the mask can be efficiently exchanged.

Second Embodiment

Figure 3:
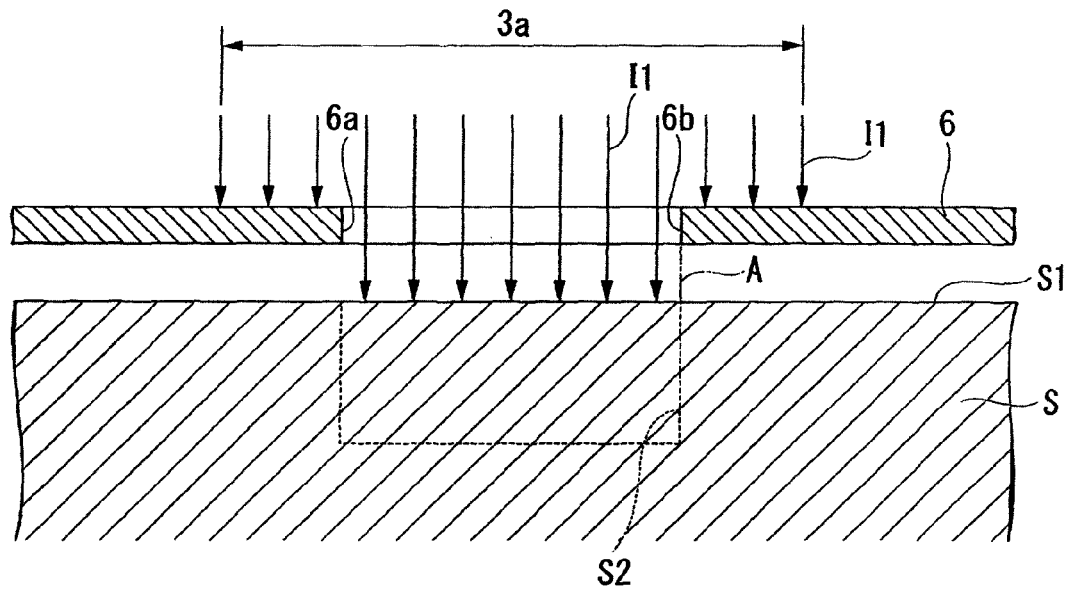
FIG. 3 is a view illustrating a first cutting step according to the first embodiment of the invention.

FIG. 3 illustrates a second embodiment of the invention. In this embodiment, the members common to the members used in the above embodiment are denoted by the same reference numerals but their description is not repeated.

Figure 5:
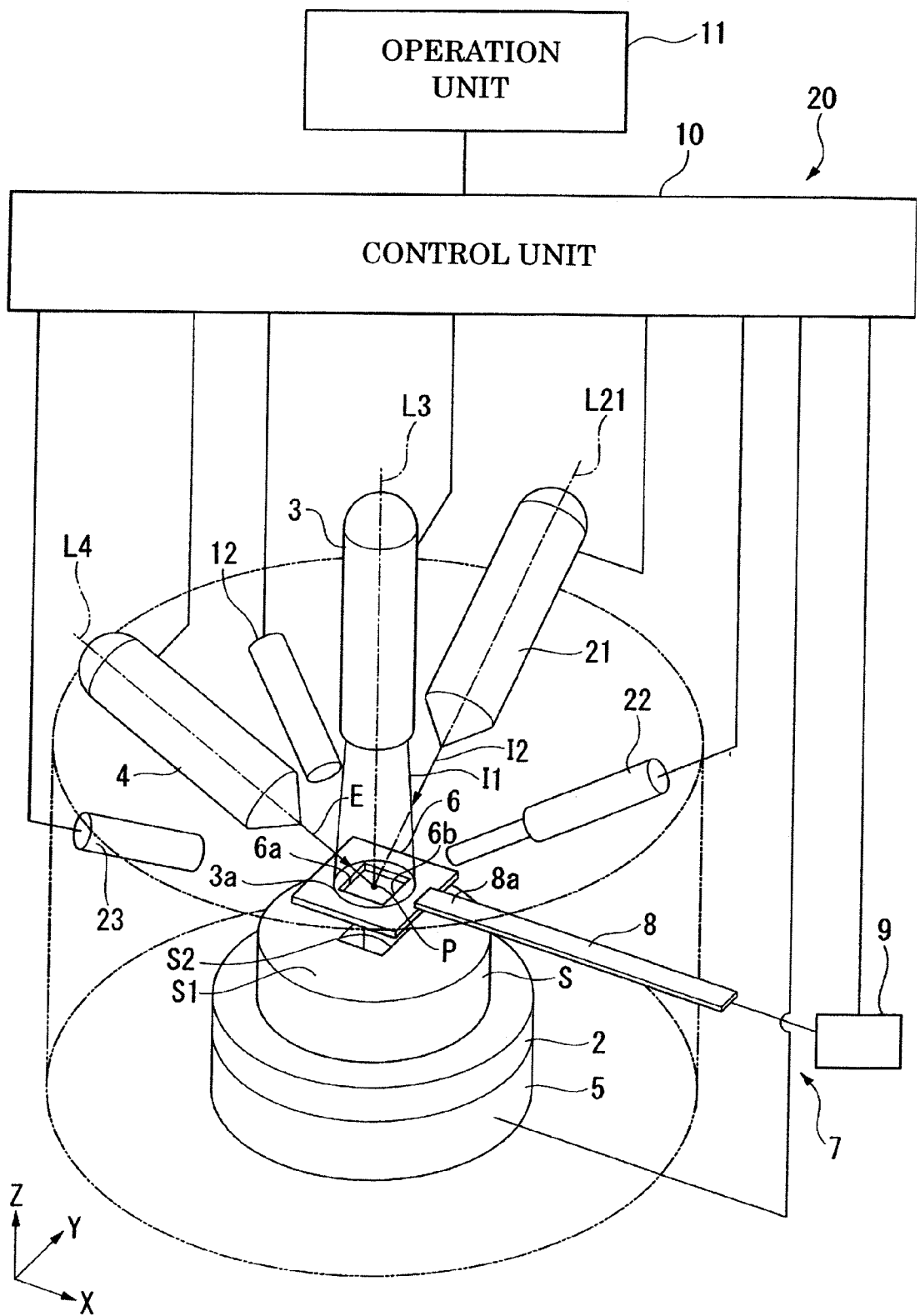
FIG. 5 is a view illustrating the constitution of the apparatus for working and observing samples according to a second embodiment of the invention.

Referring to FIG. 5, an apparatus 20 for working and observing samples of this embodiment is further provided with a second ion beam lens barrel 21 and a gas introduction mechanism 22. The second ion beam lens barrel 21 is capable of irradiating a second ion beam I2 focused with an electric current smaller than that for the first ion beam I1. The second ion beam I2 is a focused ion beam using, for example, gallium ions as an ion source. The second ion beam lens barrel 21 is capable of scanning the second ion beam I2 within the irradiation range 3a of the first ion beam I1 with the center axis L21 as a center, the center axis L21 being so set as to intersect the first ion beam lens barrel 3 and the electron beam lens barrel 4 at a point P of intersection. As will be described later, further, the second ion beam lens barrel 21 is used for finish-working the cross section of the sample that is to be observed by the electron beam lens barrel 4. It is therefore, desired that the second ion beam lens barrel 21 is so arranged that the center axis L21 thereof intersects the center axis L4 of the electron beam lens barrel 4 nearly at right angles and the second ion beam I2 irradiates along the cross section S2 of the sample as viewed from the upper side. The gas introduction mechanism 22 is for injecting a reactive gas to the sample S simultaneously with the irradiation with the second ion beam I2, and executes the selective etching for selectively etching part of the sample S or for depositing a gas component on the sample S to form a film thereof. The second ion beam lens barrel 21 and the gas introduction mechanism 22 are connected to the control unit 10, and are driven under the control of the control unit 10.

The apparatus 20 for working and observing samples is further equipped with an X-ray detector 23 capable of detecting characteristic X-rays as detection means for detecting secondarily generated substances generated from an object accompanying the irradiation with the electron beam E from the electron beam lens barrel 4. The X-ray detector 23 detects the energy and intensity of the generated characteristic X-rays, and the control unit 10 analyzes the composition on the surface of the sample from the detected spectra of the characteristic X-rays.

Figure 6:
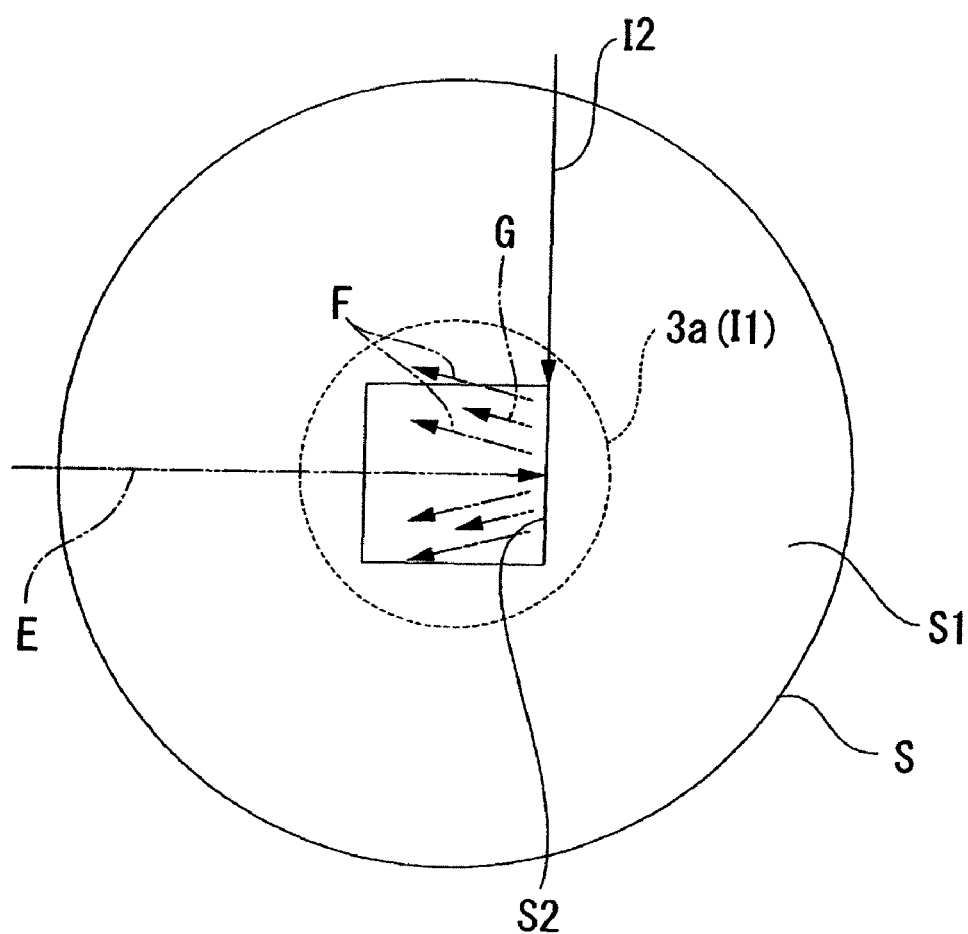
FIG. 6 is a view illustrating a second cutting step according to the second embodiment of the invention.

In the apparatus 20 for working and observing samples, after the first cutting step has been finished, the cross section S2 of the sample formed through the first cutting step is finished as the second cutting step. That is, as shown in FIG. 6, after the first cutting step has been finished, the control unit 10 drives the drive unit 9 in the mask-moving means 7 to retract the mask 6 from over the sample S. Next, the control unit 10 so sets the position for irradiating the second ion beam I2 from the ion beam lens barrel 21 as to be brought into nearly agreement with the cross section S2 of the sample, and irradiates the second ion beam I2. Therefore, the surface of the cross section S2 of the sample is more finely etched to further improve the positional precision of the cross section S2 of the sample. Further, if the selective etching is effected by introducing the reactive gas by using the gas introduction mechanism 22 while being irradiated with the second ion beam I2, only a portion of the material that is to be observed is exposed on the cross section S2 of the sample so as to be more favorably observed. In the cross section observation step, further, the secondary electrons F are detected by the secondary electron detector 12 and the characteristic X-rays G are detected by the X-ray detector 23 to identify the material exposed on the cross section S2 of the sample.

The embodiments of the invention were described above in detail with reference to the drawings. However, the concrete constitution is not limited to those of the embodiments but can be further changed and modified without departing from the gist and scope of the invention.

As the detection means, there were exemplified the secondary electron detector 12 capable of detecting secondary particles and the X-ray detector 23 capable of detecting characteristic X-rays to which only, however, the invention is not limited. For example, a secondary ion detector may be used to detect secondary ions as the secondarily generated substance. Further, as means for generating a secondary substance, there was employed the electron beam lens barrel 4 capable of irradiating the electron beam E to which only, however, the invention is in no way limited. By at least focusing the charged particle beam and scanning it on the object, the secondary substance is generated from the sample by the irradiation with the charged particle beam. Therefore, the ion beam lens barrel may be employed which is capable of irradiating the focused ion beam. In such a case, further, the second ion beam lens barrel 21 in the apparatus 20 for working and observing samples of the second embodiment may also be used as the ion beam lens barrel for generating the secondary substance. The secondary ion beam I2 irradiated from the second ion beam lens barrel was an ion beam of gallium ions, which, however, may be an inert ion beam such as a helium ion beam. By at least focusing the secondary ion beam I2 with an electric current smaller than that for the first ion beam, the cross section S2 of the sample can be finish-worked. When an inert ion beam is used as the second ion beam I2, there is provided an advantage in that the cross section S2 of the sample is less damaged than when a gallium ion beam is used.

What is claimed is:

1. An apparatus for working and observing samples, comprising:
   a sample plate on which a sample is to be placed;
   a first ion beam lens barrel capable of irradiating said sample placed on said sample plate with a first ion beam over a whole predetermined irradiation range at one time;
   a mask that can be arranged between said sample plate and said first ion beam lens barrel, and shields part of said first ion beam;
   mask-moving means capable of moving said mask on an XY-plane which intersects the irradiating direction of said first ion beam of the first ion beam lens barrel nearly at right angles;
   a charged particle beam lens barrel capable of scanning a focused beam of charged particles in said range irradiated with said first ion beam; and
   detection means capable of detecting a secondarily generated substance generated by the irradiation of said sample or said mask with said beam of charged particles from said charged particle beam lens barrel.

2. An apparatus for working and observing samples according to claim 1, wherein said first ion beam of said first ion beam lens barrel is an inert ion beam.

3. An apparatus for working and observing samples according to claim 1, further comprising a second ion beam lens barrel capable of scanning a second ion beam that is focused with an electric current smaller than that for said first ion beam within said range irradiated with said first ion beam.

4. An apparatus for working and observing samples according to claim 1, further comprising an electron beam lens barrel capable of scanning a focused electron beam having an electric current smaller than that for said first ion beam within said range irradiated with said first ion beam.

5. An apparatus for working and observing samples according to claim 1, further comprising a mask-exchanging mechanism for exchanging said mask with a mask which is different from said mask arranged in said apparatus for working and observing samples.

6. A method of working and observing a cross section, comprising:
   a mask position-adjusting step of adjusting the position of an edge end of a mask and the position for forming the cross section of said sample by arranging said mask on a sample, and by detecting a secondarily generated substance generated as a result of scanning a focused beam of charged particles;
   a first cutting step of forming a cross section of the sample at said position for forming the cross section corresponding to said edge end of said mask by etching said sample exposed through said through hole in said mask by irradiating said mask of which the position is adjusted on said sample with a first ion beam over a whole predetermined irradiation range at one time; and
   a cross section observation step of detecting the secondarily generated substance generated as a result of scanning a focused beam of charged particles on the cross section of said sample.

7. A method of working and observing a cross section according to claim 6, wherein said first cutting step uses a beam of inert ions as said first ion beam.

8. A method of working and observing a cross section according to claim 6, further comprising a second cutting step of etching the surface of the cross section of said sample by scanning a second ion beam focused with an electric current smaller than that for the first ion beam on the cross section of said sample after said first cutting step has been finished, wherein said cross section observation step is executed after said second cutting step has been finished.

9. A method of working and observing a cross section according to claim 6, wherein in said cross section observation step, the cross section of said sample is observed by scanning a focused electron beam focused with an electric current smaller than that for the first ion beam on the cross section of said sample.

10. A method of working and observing a cross section according to claim 6, wherein in said cross section observation step, the cross section of said sample is observed by scanning a second ion beam focused with an electric current smaller than that for the first ion beam on the cross section of said sample.

11. A method of working and observing a cross section according to claim 6, further comprising a step of exchanging said mask with a mask which is different from said mask arranged in said apparatus for working and observing samples.

* * * * *